United States Patent
Selover et al.

(10) Patent No.: US 9,675,272 B2
(45) Date of Patent: Jun. 13, 2017

(54) METHODS, SYSTEMS, AND DEVICES FOR GUIDING SURGICAL INSTRUMENTS USING RADIO FREQUENCY TECHNOLOGY

(71) Applicant: DePuy Synthes Products, Inc., Raynham, MA (US)

(72) Inventors: Sean P. Selover, Westport, MA (US); Joseph Hernandez, Sandwich, MA (US); John Riley Hawkins, Cumberland, RI (US); John Dieselman, Providence, RI (US); John Paul Griffin, Boston, MA (US); Jennifer DiPietro, North Easton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 373 days.

(21) Appl. No.: 13/799,414

(22) Filed: Mar. 13, 2013

(65) Prior Publication Data
US 2014/0275981 A1 Sep. 18, 2014

(51) Int. Cl.
*A61B 5/06* (2006.01)
*A61B 5/05* (2006.01)
(Continued)

(52) U.S. Cl.
CPC .............. *A61B 5/065* (2013.01); *A61B 17/70* (2013.01); *A61B 34/20* (2016.02); *A61B 5/066* (2013.01);
(Continued)

(58) Field of Classification Search
CPC ......... A61B 5/065; A61B 17/70; A61B 34/20; A61B 5/066; A61B 2034/107; A61B 2034/2051; A61B 2505/05
See application file for complete search history.

(56) References Cited

U.S. PATENT DOCUMENTS 6,205,411 B1 * 3/2001 DiGioia, III ........... A61B 17/15
 623/901
6,314,310 B1 * 11/2001 Ben-Haim et al. ........... 600/424
(Continued)

FOREIGN PATENT DOCUMENTS

WO WO 9729682 A1 * 8/1997 ........... A61B 5/0422

OTHER PUBLICATIONS

Ting et al., The study on using passive RFID tags for indoor positioning. International Journal of Engineering Business Management. 2011;3(1):9-15.

*Primary Examiner* — Long V Le
*Assistant Examiner* — Colin T Sakamoto
(74) *Attorney, Agent, or Firm* — Nutter McClennen & Fish LLP

(57) ABSTRACT

Methods, systems, and devices are provided for guiding surgical instruments using radio frequency (RF) technology. In general, the methods, systems, and devices can allow a trajectory, e.g., an angular approach, of a surgical instrument relative to a patient to be identified during use of the instrument in a surgical procedure being performed on the patient. The trajectory can be identified using a plurality of RF modules. The methods, systems, and devices can allow the trajectory to be compared to a predetermined trajectory so as to identify whether the trajectory matches the predetermined trajectory. A result of the matching can be communicated to a user of the instrument. Based on the result, the user can maintain the trajectory, e.g., if the trajectory matches the predetermined trajectory, or can adjust the trajectory to closer align the trajectory with the predetermined trajectory, e.g., if the trajectory does not match the predetermined trajectory.

20 Claims, 9 Drawing Sheets

(51) Int. Cl.
*A61B 17/70* (2006.01)
*A61B 34/20* (2016.01)
*A61B 34/10* (2016.01)

(52) U.S. Cl.
CPC . *A61B 2034/107* (2016.02); *A61B 2034/2051* (2016.02); *A61B 2505/05* (2013.01)

(56) References Cited

U.S. PATENT DOCUMENTS

| | | | | |
|---|---|---|---|---|
| 6,546,279 | B1 * | 4/2003 | Bova | A61B 8/0833 600/410 |
| 6,725,080 | B2 * | 4/2004 | Melkent et al. | 600/424 |
| 6,893,447 | B2 * | 5/2005 | Dominguez | A61B 17/0642 600/417 |
| 7,158,754 | B2 | 1/2007 | Anderson | |
| 7,835,784 | B2 * | 11/2010 | Mire et al. | 600/424 |
| 7,840,254 | B2 | 11/2010 | Glossop | |
| 8,182,491 | B2 | 5/2012 | Selover et al. | |
| 8,391,952 | B2 * | 3/2013 | Anderson | G01R 33/00 324/245 |
| 8,423,120 | B2 * | 4/2013 | Tynes | A61B 5/055 382/128 |
| 8,702,579 | B2 * | 4/2014 | Bauman | A61B 17/3403 600/1 |
| 9,125,678 | B2 * | 9/2015 | Lye | A61B 19/22 |
| 9,492,097 | B2 * | 11/2016 | Wilkes | A61B 5/042 |
| 2003/0120150 | A1 | 6/2003 | Govari | |
| 2004/0171924 | A1 * | 9/2004 | Mire et al. | 600/407 |
| 2005/0021044 | A1 * | 1/2005 | Stone | A61B 17/175 606/102 |
| 2005/0245821 | A1 * | 11/2005 | Govari | A61B 90/36 600/429 |
| 2007/0225595 | A1 * | 9/2007 | Malackowski | A61B 5/06 600/424 |
| 2008/0294258 | A1 | 11/2008 | Revie et al. | |
| 2009/0281419 | A1 | 11/2009 | Troesken et al. | |
| 2010/0036384 | A1 * | 2/2010 | Gorek et al. | 606/104 |
| 2011/0152676 | A1 | 6/2011 | Groszmann et al. | |
| 2012/0016269 | A1 | 1/2012 | Moctezuma de la Barrera | |
| 2015/0051482 | A1 * | 2/2015 | Liu | A61B 19/5244 600/424 |

* cited by examiner

METHODS, SYSTEMS, AND DEVICES FOR GUIDING SURGICAL INSTRUMENTS USING RADIO FREQUENCY TECHNOLOGY

FIELD

The present disclosure relates generally to methods, systems, and devices for guiding surgical instruments using radio frequency technology.

BACKGROUND

Spinal fixation systems can be used in orthopedic surgery to align, stabilize, and/or fix a desired relationship between adjacent vertebral bodies. Such systems typically include a spinal fixation element, such as a relatively rigid fixation rod or plate, extending along an axis along which the vertebral bodies are to be positioned and coupled to adjacent vertebrae by attaching the element to various anchoring devices, such as hooks, bolts, wires, screws, etc. The spinal fixation element can have a predetermined contour that has been designed according to the properties of the target implantation site and, once installed, the spinal fixation element holds the vertebrae in a desired spatial relationship, either until desired healing or spinal fusion has occurred, or for some longer period of time.

Spinal fixation elements can be anchored to specific portions of the vertebra. Since each vertebra varies in shape and size, a variety of anchoring devices have been developed to facilitate engagement of a particular portion of the bone. Pedicle screw assemblies, for example, typically have a shape and size configured to engage pedicle bone, which is the strongest part of the vertebrae. Such screws typically include a threaded shank configured to be threaded into a vertebra, and a head portion having a spinal fixation element receiving element, which, in spinal rod applications, is typically in the form of a U-shaped slit formed in the head for receiving the rod. A closure mechanism such as a set-screw, plug, cap, etc. can be used to lock the rod into the receiving element of the pedicle screw. In conventional use, the shank portion of each screw is threaded into a vertebra, and once properly positioned, a fixation rod is seated through the receiving element of each screw, and the rod can be locked in place by tightening the closure mechanism to securely interconnect each screw and the fixation rod. Other anchoring devices include hooks and other types of bone screws Placement of pedicle screws in a percutaneous fashion has become desirable in minimally invasive approaches to the spine. This technique generally relies heavily on a surgeon's clear understanding of a patient's local anatomy, as well as on accurate radiographic guidance technology. Generally, placement is done using a large bore needle or a cannulated drill to start an initial hole for screw placement. Pedicle screws are typically threaded in alignment with the pedicle axis and inserted along a trajectory that is determined prior to insertion of the screws. Misalignment of the pedicle screws during insertion can cause the screw body or its threads to break through the vertebral cortex and be in danger of striking surrounding nerve roots. One or more undesirable symptoms can easily arise when the screws make contact with nerves after breaking outside the pedicle cortex, such as dropped foot, neurological lesions, sensory deficits, and pain.

The placement of pedicle screws and other surgical implants for the spine and/or for other patient anatomies requires a high degree of accuracy and precision to ensure a proper trajectory for the implant. Each instrument used in the process is typically intended to be inserted along a same trajectory to ensure proper implant placement. Conventional surgical procedures for inserting pedicle screws involve recognizing landmarks along the spinal column for purposes of locating optimal screw hole entry points, approximating screw hole trajectories, and estimating proper screw hole depth. Generally, large amounts of fluoroscopy are required to determine a proper pedicle screw trajectory and to monitor the advancement of a pedicle screws through the vertebra. However, such techniques require prolonged radiation exposure to a patient and a surgeon, which risks undesirable effects of radiation exposure.

More technologically advanced systems such as the StealthStation® Treatment Guidance System, the Fluor® Nav® Virtual Fluoroscopy System (both available from Medtronic, Inc. of Minneapolis, Minn.), and related systems, seek to overcome the need for surgeons to approximate landmarks, angles, and trajectories, by assisting the surgeons in determining proper tap hole starting points, trajectories, and depths. However, these systems are extremely expensive, require significant training, are cumbersome in operation, are difficult to maintain, and are not cost effective for many hospitals and other surgical centers.

Accordingly, there remains a need for improved methods, systems, and devices for guiding surgical instruments.

SUMMARY

In one embodiment, a surgical system is provided that includes a first radio frequency module configured to be attached to a patient at a non-movable location relative to the patient such as a bone (e.g., a lateral border of a transverse process of a vertebral body), a surgical instrument having a second radio frequency module attached thereto, and a notification module configured to provide a notification to a user of the surgical instrument whether or not the surgical instrument is positioned along a predetermined trajectory to a target site within the patient based on a determined position of the second radio frequency module surgical instrument relative to the first radio frequency module.

The notification module can be configured to indicate whether or not the surgical instrument is positioned along the predetermined trajectory in a variety of ways. For example, the notification module can be configured to indicate whether or not the surgical instrument is positioned along the predetermined trajectory in at least three degrees of precision. The three degrees of precision can include the surgical instrument being along the predetermined trajectory, the surgical instrument being near but not along the predetermined trajectory, and the surgical instrument being far from the predetermined trajectory. For another example, the notification module can be configured to indicate whether or not the surgical instrument is positioned along the predetermined trajectory using at least one of an audio signal, a vibration of the surgical instrument, a light, and text. For yet another example, the notification module can be configured to repeatedly provide the notification to the user so as to repeatedly provide feedback to the user regarding whether or not the surgical instrument is positioned along the predetermined trajectory as the surgical instrument is being moved relative to the patient.

The system can include a determination module configured to repeatedly determine the position of the second radio frequency module relative to the first radio frequency module so as to repeatedly determine whether or not the surgical instrument is positioned along the predetermined trajectory.

The notification module can be configured to continuously provide the notification to the user so as to continuously provide feedback to the user regarding whether or not the surgical instrument is positioned along the predetermined trajectory.

The system can include a processor configured to be in communication with the first radio frequency module, the second radio frequency module, and the notification module, configured to determine the position of the surgical instrument relative to the first radio frequency module, and configured to cause the notification module to provide the notification.

In another aspect, a surgical method is provided that includes attaching a first radio frequency module to a patient at a non-movable location relative to the patient, e.g., a bone, and moving a surgical instrument toward the patient. The surgical instrument has a second radio frequency module attached thereto. The method can also include determining a position of the second radio frequency module relative to the first radio frequency module so as to determine whether or not the surgical instrument is being moved along a predetermined trajectory to a target site within the patient, and providing a notification to a user of the surgical instrument whether or not the surgical instrument is being moved along the predetermined trajectory.

The notification can be provided in a variety of ways. Providing the notification can include indicating whether or not the surgical instrument is positioned along the predetermined trajectory in one of at least three degrees of precision. The three degrees of precision can include the surgical instrument being along the predetermined trajectory, the surgical instrument being near but not along the predetermined trajectory, and the surgical instrument being far from the predetermined trajectory. Providing the notification can include at least one of sounding an audio signal, vibrating the surgical instrument, illuminating a light, and displaying text.

The method can vary in any number of ways. For example, the method can include determining the predetermined trajectory by positioning the surgical instrument at a desired trajectory angle relative to the target site and setting a spatial relationship between the first radio frequency module and the second radio frequency module when the surgical instrument is at the desired trajectory angle as the predetermined trajectory. The predetermined trajectory can be reset by positioning the surgical instrument at a second desired trajectory angle relative to the target site and setting a spatial relationship between the first radio frequency module and the second radio frequency module when the surgical instrument is at the second desired trajectory angle as the predetermined trajectory. For another example, the method can include determining the predetermined trajectory by comparing a pre-operative image of the patient including the target site with the location of the first radio frequency module within the patient. For yet another example, the method can include attaching a third radio frequency module to the patient at another non-movable location relative to the patient, and determining the predetermined trajectory by comparing a pre-operative image of the patient including the target site with the location of the first radio frequency module and the location of the third radio frequency module within the patient. The target site can include a spinal disc level, the non-movable location can include a first vertebra above the disc level, and the second non-movable location can include a second vertebra below the disc level. For another example, the notification can be continuously provided to the user so as to continuously provide feedback to the user regarding whether or not the surgical instrument is being moved along the predetermined trajectory as the surgical instrument is being moved relative to the patient. For yet another example, the method can include repeatedly determining the position of the second radio frequency module relative to the first radio frequency module so as to repeatedly determine whether or not the surgical instrument is being moved along the predetermined trajectory. The notification can be continuously provided to the user so as to continuously provide feedback to the user regarding whether or not the surgical instrument is being moved along the predetermined trajectory. For another example, the method can include moving a second surgical instrument toward the patient. The surgical instrument can have a third radio frequency module attached thereto. The method can also include determining a position of the third radio frequency module relative to the first radio frequency module so as to determine whether or not the surgical instrument is being moved along the predetermined trajectory, and providing a notification to a user of the second surgical instrument whether or not the second surgical instrument is positioned along the predetermined trajectory.

BRIEF DESCRIPTION OF DRAWINGS

This invention will be more fully understood from the following detailed description taken in conjunction with the accompanying drawings, in which.

DETAILED DESCRIPTION

Figure 1:
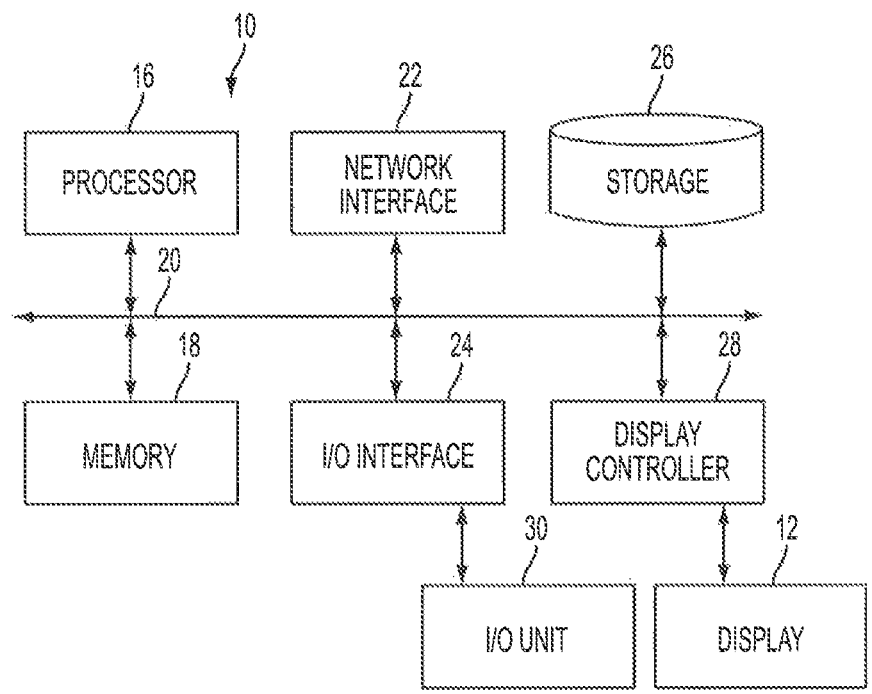
FIG. 1 is a schematic view of an embodiment of a computer system.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods, systems, and devices are provided for guiding surgical instruments using radio frequency (RF) technology. In general, the methods, systems, and devices can allow a trajectory of a surgical instrument relative to a patient, e.g., an angular approach of the instrument relative to the patient, to be identified during use of the instrument in a surgical procedure being performed on the patient. The methods, systems, and devices can allow the trajectory to be compared to a predetermined trajectory so as to identify whether the trajectory matches the predetermined trajectory. The predetermined trajectory can include an optimized trajectory of the instrument for accessing the patient, e.g., a target site at the patient such as a bone (e.g., a vertebra, a patella, etc.), a soft tissue (e.g., an anterior cruciate ligament, etc.), and an organ (e.g., a stomach, a bladder, etc), at an angle effective for performance of the procedure using the instrument and/or for the instrument safely and/or efficiently accessing the target site, e.g., avoiding nerves, avoiding a device previously implanted within the patient, passing through a minimum amount of tissue to reach the target site, etc. A result of the matching can be communicated to a user of the instrument, e.g., a surgeon, a robotic arm handling the instrument, a surgical assistant, etc. Based on the result, the user can maintain the trajectory, e.g., if the trajectory matches the predetermined trajectory, or can adjust the trajectory to more closely align the trajectory with the predetermined trajectory, e.g., if the trajectory does not match the predetermined trajectory. The result can be communicated to the user in real time with use of the instrument in the procedure. The trajectory can thus be adjusted in real time, which can help allow the instrument to be efficiently and quickly advanced to the target site and/or can help prevent the instrument from damaging tissue, impinging on a nerve, needing to be reinserted into the patient, and/or deviating from a safe approach angle. The trajectory of the instrument can be repeatedly identified during use of the instrument in the procedure, thereby allowing the trajectory to be repeatedly compared with the predetermined trajectory. The user can thus repeatedly receive information regarding the trajectory as compared to the predetermined trajectory, thereby allowing the trajectory to be adjusted throughout use of the instrument should the trajectory ever stray from the predetermined trajectory.

The trajectory can be identified using a plurality of RF modules, which can be relatively inexpensive, can be used with relatively small power requirements, and can be biocompatible so as to be able to be configured for safe attachment to a patient, e.g., attached to a skin surface thereof or implanted therein. The predetermined trajectory can be identified using at least some of the plurality of RF modules, which can facilitate comparison of the trajectory with the predetermined trajectory and/or can allow the trajectory to be identified during performance of the surgical procedure without requiring fluoroscopy during the surgical procedure. In robotic-assisted surgery, the predetermined trajectory can be used to guide robotically-controlled instrument(s) along the predetermined trajectory, which can help provide very precise positioning of the robotically-controlled instrument(s) and can facilitate human notification and correction of any deviations of the robotically-controlled instrument(s) from the predetermined trajectory.

The systems and methods disclosed herein can be implemented using one or more computer systems. FIG. 1 illustrates one exemplary embodiment of a computer system 10. As shown, the computer system 10 can include one or more processors 16 which can control the operation of the computer system 10, such as by executing an operating system (OS), a basic input/output system (BIOS), device drivers, application programs, and so forth. The processor(s) 16 can include any type of microprocessor or central processing unit (CPU), including programmable general-purpose or special-purpose microprocessors and/or any one of a variety of proprietary or commercially available single or multi-processor systems. The computer system 10 can also include one or more memories 18, which can provide temporary storage for code to be executed by the processor(s) 16 or for data acquired from one or more users, storage devices, and/or databases. The memory 18 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 10 can be coupled to a bus system 20. As will be appreciated by a person skilled in the art, the illustrated bus system 20 is an abstraction that represents any one or more separate physical busses, communication lines/interfaces, and/or multi-drop or point-to-point connections, connected by appropriate bridges, adapters, and/or controllers.

The computer system 10 can also include one or more network interfaces 22, one or more input/output (I/O) interfaces 24, one or more storage devices 26, and one or more display controllers 28. The network interface(s) 22 can enable the computer system 10 to communicate with remote devices, e.g., other computer systems, over a network. Examples of the network interface 22 include remote desktop connection interfaces, Ethernet adapters, and other local area network (LAN) adapters. The I/O interface(s) 24 can include one or more interface components to connect the computer system 10 with other electronic equipment. For non-limiting example, the I/O interface(s) 24 can include high speed data ports, such as universal serial bus (USB) ports, 1394 ports, etc. Additionally, the computer system 10 can be accessible to a human user, and thus the I/O interface(s) 24 can include displays, speakers, keyboards, pointing devices, and/or various other video, audio, or alphanumeric interfaces. The I/O interface 24 can facilitate communication between one or more I/O units 30. A person skilled in the art will appreciate that the system 10 can be configured to communicate with a variety of I/O units 30. Examples of input units include a keyboard, a touch screen, a mouse, a joystick, and a pointing device. Examples of output units includes a speaker, a printer, a scanner, a removable memory, and the various other components of the system 10. The storage device(s) 26 can include any conventional medium for storing data in a non-volatile and/or non-transient manner. The storage device(s) 26 can thus hold data and/or instructions in a persistent state, i.e., the value is retained despite interruption of power to the computer system 10. The storage device(s) 26 can include one or more hard disk drives, flash drives, USB drives, optical drives, various media cards, and/or any combination thereof and can be directly connected to the computer system 10 or remotely connected thereto, such as over a network. The display controller(s) 28 can include a video processor and a video memory, and can generate data such as images and/or text to be displayed on a display 12 in accordance with instructions received from the processor 16.

The elements illustrated in FIG. 1 can be some or all of the elements of a single physical machine. In addition, not all of the illustrated elements need to be located on or in the same physical machine. Exemplary embodiments of computer systems include desktop computers, workstations, minicomputers, laptop computers, tablet computers, personal digital assistants (PDAs), mobile phones, smartphones, and the like.

A computer system can include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

One or more software modules can be executed by the system 10 to facilitate human interaction with the system 10. These software modules can be part of a single program or one or more separate programs, and can be implemented in a variety of contexts, e.g., as part of an operating system, a device driver, a standalone application, and/or combinations thereof. A person skilled in the art will appreciate that any software functions being performed by a particular software module can also be performed by any other module or combination of modules.

Figure 2:
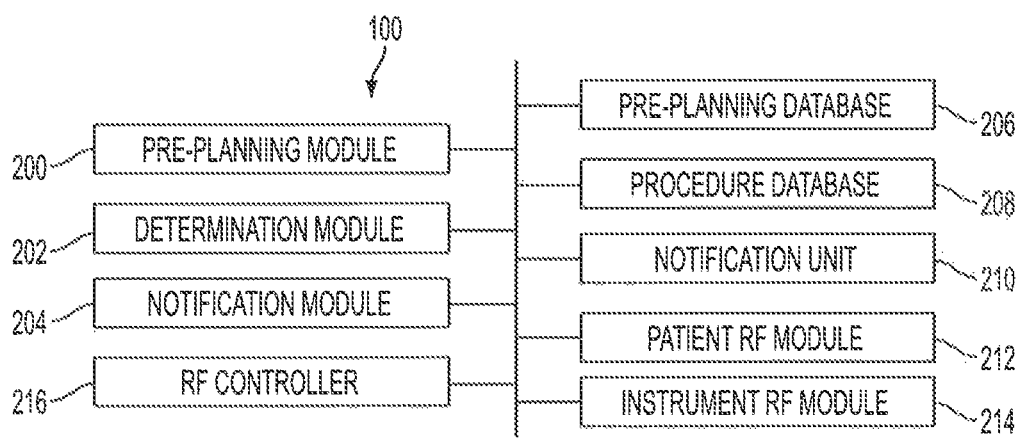
FIG. 2 is a schematic diagram of an embodiment a trajectory determination system.

FIG. 2 is a schematic block diagram of one exemplary embodiment of a trajectory determination system 100. The system 100 can includes a plurality of modules, discussed further below, which can each be implemented using one or more computer systems of the type described above. The system 100 can be implemented on a single computer system, or can be distributed across a plurality of computer systems. The system 100 can also include a plurality of databases, which can be stored on and accessed by computer systems. It will be appreciated by a person skilled in the art that any of the modules or databases disclosed herein can be subdivided or can be combined with other modules or databases.

Figure 3:
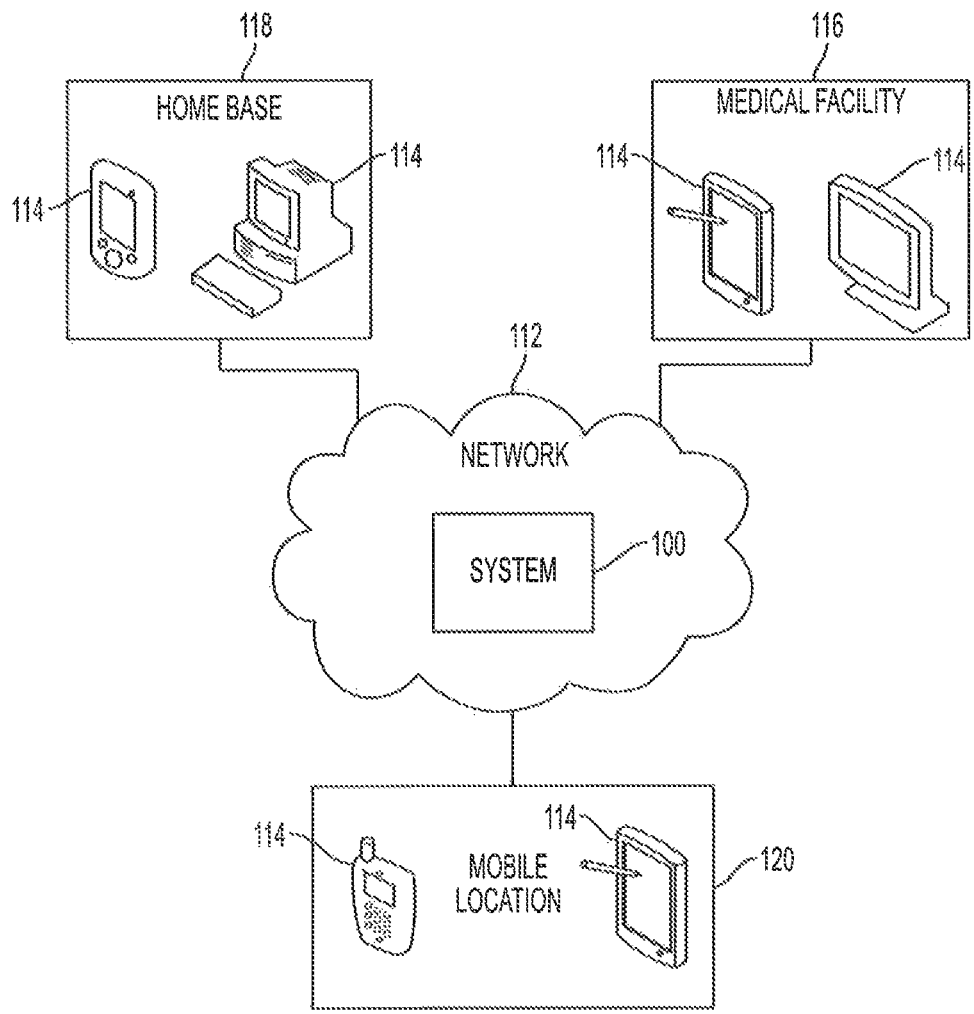
FIG. 3 is a schematic diagram of an embodiment of a network system including the trajectory determination system of FIG. 2.

Any of a variety of parties can access, interact with, control, etc. the system 100 from any of a variety of locations. For non-limiting example, as shown in an embodiment illustrated in FIG. 3, the system 100 can be accessible over a network 112 (e.g., over the Internet via cloud computing, over a private local area network (LAN), etc.) from any number of client stations 114 in any number of locations such as a medical facility 116 (e.g., a hospital, an operating room (OR), a nurse's station, a medical device distribution facility, a medical device company, a hospital's sterilization, records, or billing departments, etc.), a home base 118 (e.g., a surgeon's home or office, etc.), a mobile location 120, and so forth. The client station(s) 114 can access the system 100 through a wired and/or wireless connection to the network 112. In an exemplary embodiment, at least some of the client terminal(s) 114 can access the system 100 wirelessly, e.g., through Wi-Fi connection(s), which can facilitate accessibility of the system 100 from almost any location in the world. As shown in FIG. 3, the medical facility 116 includes client stations 114 in the form of a tablet and a computer touch screen, the home base 118 includes client stations 114 in the form of a mobile phone having a touch screen and a desktop computer, and the mobile location 120 includes client stations 114 in the form of a tablet and a mobile phone, but the medical facility 116, the home base 118, and the mobile location 120 can include any number and any type of client stations. In an exemplary embodiment, the system 100 can be accessible by a client terminal via a web address and/or a client application (generally referred to as an "app").

Referring again to FIG. 2, the system 100 can include a pre-planning module 200, a determination module 202, and a notification module 204. Any of the pre-planning module 200, the determination module 202, and the notification module 204 can be used independently from one another and can be used in combination with any one or more of the other modules 200, 202, 204. Although each of the modules 200, 202, 204 is illustrated in FIG. 2 as a singular module, each of the modules 200, 202, 204 can include any number of component modules, e.g., one, two, three, etc., the same or different from any of the other modules 200, 202, 204. Further, as mentioned above, it will be appreciated by a person skilled in the art that any of the modules 200, 202, 204, and any of their various component modules, can be subdivided or can be combined with other modules, including modules illustrated in FIG. 2 as being in different ones of the modules 200, 202, 204. The system 100 can also include at least one patient RF module 212 and at least one instrument RF module 214, which can each be configured to transmit information via radio frequency to the system 100 that can be analyzed by one or more of the pre-planning module 200, the determination module 202, and the notification module 204, as discussed further below.

The system 100 can include a pre-planning database 206 configured to be accessible by the pre-planning module 200 and configured to store pre-planning data. The system 100 can also include a procedure database 208 configured to be accessible by the determination module 202 and the notification module 204 and configured to store procedure data. Each of the databases 206, 208 can include any number of component databases, e.g., one, two, three, etc., the same or different from any of the other databases 206, 208. As mentioned above, it will be appreciated by a person skilled in the art that any of the databases 206, 208, and any of their various component databases, can be subdivided or can be combined with other databases, including databases illustrated in FIG. 2 as being in different ones of the databases 206, 208. Any portion of any of the databases 206, 208 can be configured to be accessed by any one or more of the modules 200, 202, 204. Although the system 100 in the illustrated embodiment stores data in database(s), any of the systems disclosed herein can store data in database(s) and/or in other data organization structure(s).

The system 100 can also include a notification unit 210 configured to be accessible by the notification module 204 and configured to provide a notification to a user of the system 100 of information related to performance of a surgical procedure on a patient. Although the notification unit 210 is illustrated in FIG. 2 as a singular unit, the notification unit can 210 include any number of notification units, e.g., one, two, three, etc. Examples of the notification unit 210 include a light, a speaker, a vibration unit, and a display.

In general, and as discussed further below, the pre-planning module 200 can be configured to facilitate determination of a trajectory of a surgical instrument relative to a patient on which the surgical instrument is to be used in performance of a surgical procedure. The determined trajectory can thus be a predetermined trajectory that is determined before the surgical instrument is actually used on the patient and/or is actually advanced into the patient's body. The predetermined trajectory can be determined using at least the patient RF module(s) 212, as discussed further below. The pre-planning module 200 can be configured to store the predetermined trajectory in the pre-planning database 206.

The determination module 202 can be configured to determine whether a surgical instrument being used to perform an actual surgical procedure on the patient has a trajectory relative to the patient that is aligned with the predetermined trajectory stored in the pre-planning database 206. The determination module 202 can thus be configured to compare the predetermined trajectory with an actual trajectory so as to determine a deviance of the trajectory from the predetermined trajectory. The determination module 202 can be configured to perform the comparison using the patient RF module(s) 212 and the instrument RF module(s) 214, e.g., using an RF positioning technique such as radio frequency identification (RFID) localization, RFID triangulation, RFID zoning, etc.

Based on whether the trajectory is aligned with the predetermined trajectory, e.g., based on the determination made by the determination module 202, the notification module 204 can be configured to cause the notification unit 210 to provide a notification indicating the alignment, or misalignment, of the trajectory with the predetermined trajectory. The notification can include a visual, tactile, and/or auditory indication as to whether a surgical instrument being used in performing the surgical procedure has a trajectory relative to the patient that is aligned with the predetermined trajectory. The notification can thus allow the surgical instrument's actual trajectory to be maintained, if the trajectory aligns with the predetermined trajectory, or to be adjusted to more closely align with the predetermined trajectory, if the trajectory is offset from the predetermined trajectory. The surgical instrument can thus be more likely to be safely and optimally used in the surgical procedure, to be quickly adjusted to an optimal angle relative to the patient, and/or to be less likely to cause tissue damage or otherwise harm the patient by unintentionally contacting or otherwise impinging on nerves, soft tissue, etc. The determination module 202 can be configured to repeatedly compare the trajectory with the predetermined trajectory such that as the instrument moves relative to the patient, the notification module 204 can be configured to cause the notification unit 210 to provide notification if the instrument ever veers from the predetermined trajectory.

It will be appreciated by a person skilled in the art that the system 100 can include security features such that the aspects of the system available to any particular user can be determined based on the identity of the user and/or the location from which the user is accessing the system. To that end, each user can have a unique username, password, and/or other security credentials to facilitate access to the system 100. The received security parameter information can be checked against a database of authorized users to determine whether the user is authorized and to what extent the user is permitted to interact with the system 100, view information stored in the system 100, and so forth. Examples of parties who can be permitted to access the system 100 include surgical technicians, surgeons, nurses, and operating room directors.

In an exemplary embodiment, users of the system 100 can include medical practitioners who treat patients in an operating room (OR) or other surgical procedure performance setting. In some embodiments, the system 100 can be accessible by users other than medical practitioners, such as by medical administrators, medical students, etc. Different users can have access to different portions of the system 100, as mentioned above regarding security features. For example, the system 100 can be configured to allow surgeons to access all of the modules 200, 202, 204 and to allow other operating room personnel to access only the determination module 202. A user can have access to only a portion of a module, e.g., to only a subset of component modules within any one or more of the modules 200, 202, 204.

Figure 4:
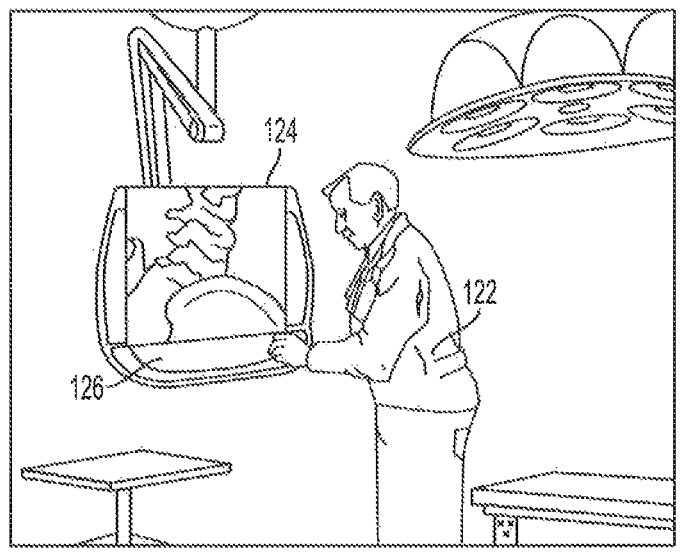
FIG. 4 is a perspective view of an embodiment of a client terminal in an OR setting that communicates with the trajectory determination system of FIG. 2.
Figure 4A:
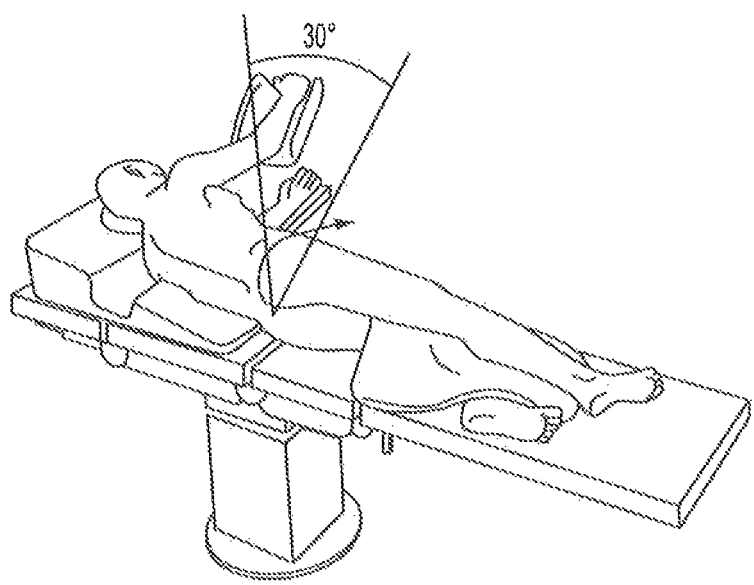
FIG. 4A is a perspective view of an embodiment of a patient on a bed in a surgical setting.
Figure 4B:
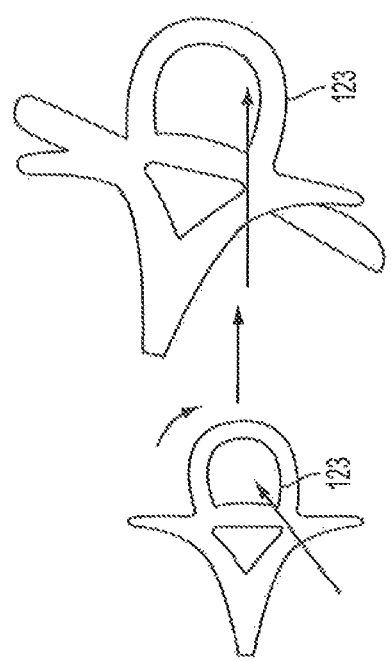
FIG. 4B is a series of perspective views of a spine of the patient of FIG. 4A.

FIG. 4 illustrates an embodiment of a user 122 accessing the system 100 in an OR via a client terminal in the form of a computer including a processor (not shown), a display 124, and a keyboard 126. In the illustrated embodiment, the user 122 is viewing a pre-operative image of a patient's spine in connection with a spinal procedure being performed in the OR, e.g., disc fusion, disc removal, cage insertion, etc. For some spinal surgical procedures, a trajectory of lateral approach can be very important so as to access a target vertebra while avoiding nerve damage, and a patient's position can be of particular importance to the surgery's duration and ultimate success. During lateral interbody surgery, for example, it can be advantageous to align a representative plane of a superior endplate of a patient's inferior vertebra to vertical plumb, and it can be advantageous to align a mid frontal plane of the patient's interbody space to vertical plumb. In other words, it can be advantageous to position a center of the patient's vertebral disc, as well as endplates of the vertebrae, straight down from a perspective of a surgeon performing the surgery. Implantation of one or more percutaneous screws while a patient remains in a lateral position is an example of a spinal surgical procedure in which precise trajectory and patient positioning is important. As shown in FIGS. 4A and 4B, lining up a patient's pedicle 123 for direct horizontal pedicle screw placement can be about a 30° rotation. FIG. 4B shows the pedicle 123 in an initial position, e.g., at 30°, on the left, and in a rotated position, e.g., at 0° (horizontal), on the right. In an exemplary embodiment, the system 100 can be configured to inform medical personnel of a relation of an operative instrument to the 30° trajectory, or the system 100 can inform the medical personnel during surgical bed positioning of the patient's pedicle relation to horizontal. The system 100 can, however, be used to simulate other types of surgical procedures and view other data.

Figure 5:
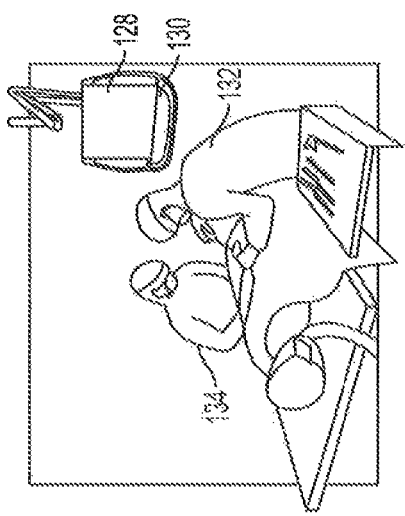
FIG. 5 is a perspective view of another embodiment of a client terminal in an OR setting that communicates with the trajectory determination system of FIG. 2.

In an exemplary embodiment, as shown in FIG. 4, an OR has a single display or user interface configured to display information from the system 100 for consultation during a surgical procedure performed in the OR. The display or user interface can be located in the OR, or can be in a nearby area visible from the OR. FIG. 5 illustrates an embodiment of an OR setting in which the system 100 can be accessed via a client terminal in the form of a computer including a processor (not shown), a display 128, and a keyboard 130. In the illustrated embodiment, a surgeon 132 and medical support personnel 134 can all view the display 128, which can help all OR personnel be aware of information provided by the system 100 and any other information provided on the display 128 that can help the personnel track the procedure, be better informed of their duties, and help quickly notice any anomalies.

Figure 6:
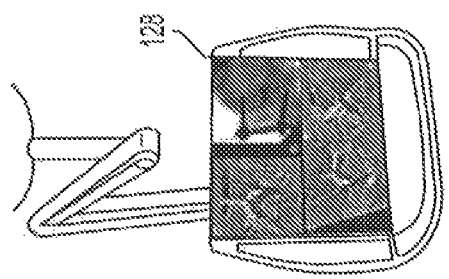
FIG. 6 is a perspective view of an embodiment of a client terminal showing surgical procedure data received from the trajectory determination system of FIG. 2.

Various types of data gathered and/or analyzed by the system 100 during and before a surgical procedure can be displayed on the display 128. FIG. 6 illustrates the display 128 showing examples of various types of data, namely three images of a surgical site captured during a surgical procedure at a same time from three different perspectives. Another portion of the display 128 (top right quadrant) shows a pre-operative patient x-ray of the surgical site. By allowing the user to view different data simultaneously, the user can better evaluate success of the surgical procedure, including proper instrument trajectory angles. Different types of data can be displayed on the display 128 other than the information shown on the display 128, such as time durations of certain steps of the surgical procedure, a total time duration of the surgical procedure, notification(s) triggered by the notification module 204, pre-op images of the patient stored in the pre-planning database 206, etc.

Figure 7:
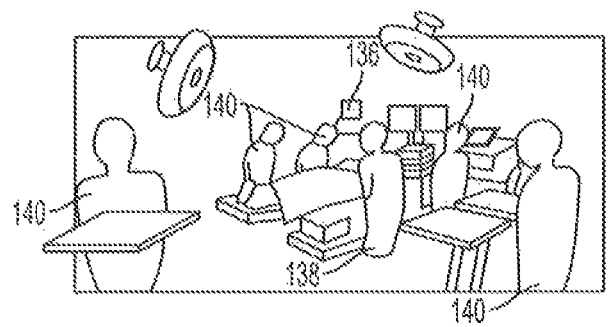
FIG. 7 is a perspective view of yet another embodiment of a client terminal in an OR setting that communicates with the trajectory determination system of FIG. 2.

FIG. 7 illustrates another embodiment of an OR setting in which the system 100 can be accessed via a client terminal in the form of a computer including a processor (not shown) and a display 136 located at a position easily seen from all or nearly all positions within the OR by a surgeon 138 and medical support personnel 140.

Although the illustrated embodiments of FIGS. 4, 5 and 7 each include only one display for the system 100 in an OR, any number of displays for the system 100 can be provided in an OR. Providing a plurality of displays can allow more information to be easily accessible to medical personnel in the OR at any given time, can help focus medical personnel by allowing for different medical personnel to have dedicated displays providing information most useful for their particular job, and/or can reduce surgeon fatigue by allowing the surgeon to position themselves differently than if the displays were not available. Additionally, any one or more displays for the system 100 in the OR can be configured to display a plurality of views, e.g., have picture-in-picture capability (e.g., two different camera angles of the same surgical site) and/or provide overlays of data (e.g., an illustrated trajectory line over a pre-operative image of a patient's anatomy).

Various types of data gathered and/or analyzed by the system 100 can be provided to a user of the system 100 via the notification unit 210, e.g., displayed on a display and/or otherwise made available to medical personnel in the OR such as by other visual indicator (e.g., by blinking light on a surgical instrument, etc.), motion (e.g., by vibration of a surgical instrument, etc.), and sound (e.g., by audio beep from a speaker, etc.). By providing non-auditory feedback alone or in combination with visual feedback, the feedback can be less likely to be lost or overlooked in a noisy OR environment.

The pre-planning module 200 can generally provide users of the system 100 with an interface for creating and storing data related to a surgical procedure to be performed on a patient before the surgical procedure is performed on the patient. In an exemplary embodiment, only surgeons authorized to perform surgery can access the pre-planning module 200, which can help ensure that a patient's pre-surgery planning remains consistent with the performing surgeon's preferences, plans, etc. The pre-planning database 206 can be configured to store data created and/or collected by the pre-planning module 200. The data stored in the pre-planning database 206 can be used by the determination module 202 in making various determinations during and/or after performance of an actual surgical procedure, as discussed further below.

As will be appreciated by a person skilled in the art, various types of data related to a patient can be gathered prior to performance of a surgical procedure on the patient and stored in the pre-planning database 206. This data can be used in planning the surgical procedure and/or during performance of the surgical procedure to help the surgical procedure be safely and efficiently performed on the patient. Examples of data that can be stored in the pre-planning database 206 include data related to the patient, such as one or more pre-operative images of a targeted area of the patient for surgery, number of the patient RF modules 212 implanted in the patient, type of each patient RF module 212 implanted in the patient, weight, medical insurance information, age, medical history of the patient, prior surgery performed on the patient, drug allergies, drug interactions, physiological data, current medical diagnoses, bone density, blood type, cumulative radiation exposure (e.g., a total amount of radiation the patient has been exposed to through x-rays and/or other radiation sources), medications currently being taken by the patient, etc., and data related to surgical personnel, such as an identification of which and how many medical personnel are to be present in the OR at any given time, how long each medical personnel member is scheduled to be present during the surgical procedure, number of personnel changes during performance of the surgical procedure, cumulative radiation exposure (e.g., a total amount of radiation each of the personnel members has been exposed to through x-rays and/or other radiation sources), etc. Having a cumulative radiation exposure amount for the patient and/or for the surgical personnel can help encourage reduction of a person's radiation exposure and help ensure that the person is not exposed to radiation beyond an acceptable level within a certain period of time.

In an exemplary embodiment, at least one or more pre-operative images of a targeted area of the patient for surgery can be stored in the pre-planning database 206. The pre-operative image(s) can include any number of images and can be gathered in any one or more ways, as will be appreciated by a person skilled in the art. Examples of such images include x-rays, magnetic resonance imaging (MRI) images, x-ray computed tomography (CT) scans, etc. In an exemplary embodiment, prior to taking of at least one of the pre-operative images of the patient, the one or more patient RF modules 212 can be attached to the patient. At least one of the pre-operative images can thus include an image of the one or more patient RF modules 212. The pre-planning module 200 and/or the determination module 202 can use the pre-operative image(s) including the one or more patient RF module 212 therein to help pre-determine, before performance of the surgical procedure, an optimal trajectory of a surgical instrument relative to the patient and/or help determine whether a surgical instrument being used in the surgical procedure is aligned with the optimal trajectory. As discussed further below, in some embodiments, a single one of the patient RF modules 212 can be attached to the patient, while in other embodiments, a plurality of the patient RF modules 212 can be attached to the patient.

Each of the one or more patient RF modules 212 configured to be attached to the patient can have a variety of sizes, shapes, and configurations. If a plurality of the patient RF modules 212 are attached to the patient, each of the plurality of patient RF modules 212 can be the same as or different from any one or more of the other patient RF modules 212. In general, the at least one patient RF module 212 can be configured to be attached to a patient and to wirelessly communicate using radio frequency electromagnetic fields, which can allow the patient RF module(s) 212 to be queried without requiring a visual line of sight to the patient RF module(s) 212. The patient RF module(s) 212 can be configured to wirelessly transmit a signal in response to a wireless signal transmitted by an external source, such as an RF controller 216 (e.g., a handheld RF wand or controller, an RF controller coupled to a stationary object such as a table or a wall, etc.) The signal transmitted by each of the patient RF module(s) 212 can include one or more types of data associated with the patient RF module(s) 212, such as RF-specific information (e.g., an identifier uniquely identifying the RF module such as an identification code or name, date of the RF module's attachment to the patient, etc.) and/or patient-specific information (e.g., an identifier uniquely identifying the patient such as an identification code or name, a type of surgical procedure to be performed on the patient, a timestamp and/or datestamp of the RF query of the patient RF module, etc.). The data transmitted by each of the patient RF module(s) 212 can be stored in an on-board memory of the patient RF module(s) 212. The patient RF module(s) 212 can each include an on-board power source, e.g., a battery, or can be powered by an external source. The patient RF module(s) 212 can be biocompatible so as to be configured to be safely attached to the patient. In an exemplary embodiment, the patient RF module(s) 212 can be biocompatible, can be configured to be implanted within a patient, and can lack an on-board power source. Examples of patient RF module(s) 212 include RFID tags that include an emitter configured to emit RF signals and a receiver configured to receive RF signals. The measurement/sensing of Relative Signal Strength of a given RFID module can be used as an analog for target distance by comparison with known/calibrated/expected signal strength from a target at that distance. Range finding can be performed by RF reflective or echo transmitting range finding. Other forms of electro-magnetic-radiation can be used for range finding, e.g., infra-red; optical laser; non-EMR pressure wave sensors such as ultra sound sensors can be used for target ranging; etc. The known distances from transmitters to targets can be combined algebraically and used for continuous update of the surgical instrument's position and trajectory. Using RFID tags for object position determination is further discussed in Ting et al., "The Study on Using Passive RFID Tags for Indoor Positioning," *International Journal of Engineering Business Management*, Vol. 3, No. 1 (2011), pp. 9-15.

The one or more patient RF modules 212 can be attached to the patient in a variety of ways. In an exemplary embodiment, the patient RF module(s) 212 can be attached to an exterior surface of the patient, e.g., attached to the patient's skin. The patient RF module(s) 212 can be attached to the exterior surface of the patient in a variety of ways, such as by using one or more attachment elements such as a biocompatible adhesive (e.g., a glue), medical tape, etc. Being attached to an exterior surface of the patient can facilitate temporary attachment of the patient RF module(s) 212 to the patient by allowing the patient RF module(s) 212 to be easily unattached from the patient with minimal patient discomfort and without requiring surgery to unattach the patient RF module(s) 212.

In another exemplary embodiment, the patient RF module(s) 212 can be attached to a patient by being implanted within a patient's body. The patient RF module(s) 212 can be implanted in a variety of ways using a variety of surgical techniques, as will be appreciated by a person skilled in the art. The one or more patient RF modules 212 can be implanted within the patient at a variety of locations. In an exemplary embodiment, the one or more patient RF modules 212 can be attached to a non-movable location relative to the patient, e.g., attached to a bone or a tooth. The non-movable location can be adjacent a target surgical site within the patient, e.g., attached to a vertebra being operated on, attached to a vertebra next to a vertebra being operated on, attached to a femur near a reattachment site for a damaged anterior cruciate ligament (ACL), etc. Attaching the patient RF module(s) 212 at a non-movable location relative to the patient can allow the patient RF module(s) 212 to remain at fixed position(s) relative to the target surgical site, even if the patient shifts position relative to a surgeon or other medical personnel, to instruments, to an operating table, etc. The patient RF module(s) 212 can thus provide consistent locational information relative to the surgical site during performance of the surgical procedure and/or as compared to pre-operative images of the patient showing the patient RF module(s) 212 and/or showing the target surgical site. Implanting the one or more patient RF modules 212 can allow the implanted patient RF module(s) 212 to be used in performance of multiple, different surgical procedures. The patient RF module(s) 212 can be attached to the patient within the patient in a variety of ways, such as by using any one or more attachment elements such as a biocompatible adhesive (e.g., a glue), a pin, a screw, etc.

In some embodiments, the patient RF module(s) 212 can be implanted in the patient during a same surgical procedure in which the patient RF module(s) 212 are used in determining a trajectory of a surgical instrument being used in the procedure. This can reduce a number of surgical procedures performed on the patient and/or can allow a trajectory to be predetermined for a surgical instrument being used in performing the procedure, as discussed further below. In other embodiments, the patient RF module(s) 212 can be implanted within the patient in a surgical procedure prior to the surgical procedure in which the patient RF module(s) 212 are used in determining a trajectory of a surgical instrument being used in the procedure. This can facilitate pre-planning of the surgical procedure by allowing one or more pre-operative images of the patient having the patient RF module(s) 212 implanted therein be taken outside an OR, e.g., in a non-surgical setting, by providing more time for a surgeon to plan the surgical procedure between implantation of the patient RF module(s) 212 and performance of the surgical procedure, and allow a trajectory to be predetermined for a surgical instrument to be used in performing the procedure, as discussed further below.

If a plurality of patient RF modules 212 are attached to a patient, all of the patient RF modules 212 can be externally attached to the patient, all of the patient RF modules 212 can be implanted within the patient, or at least one of the patient RF modules 212 can be externally attached and at least one of the patient RF modules 212 can be implanted. Attaching a plurality of patient RF modules 212 to the patient can facilitate triangulation of the patient RF modules 212 with the one or more instrument RF modules 214. In general, a greater number of instrument RF modules 214 corresponds to a greater accuracy of triangulation. The triangulation can provide positional information in multiple planes, e.g., X and Y planes to approximate a planar location and a Z plane to indicate a depth location.

Figure 8:
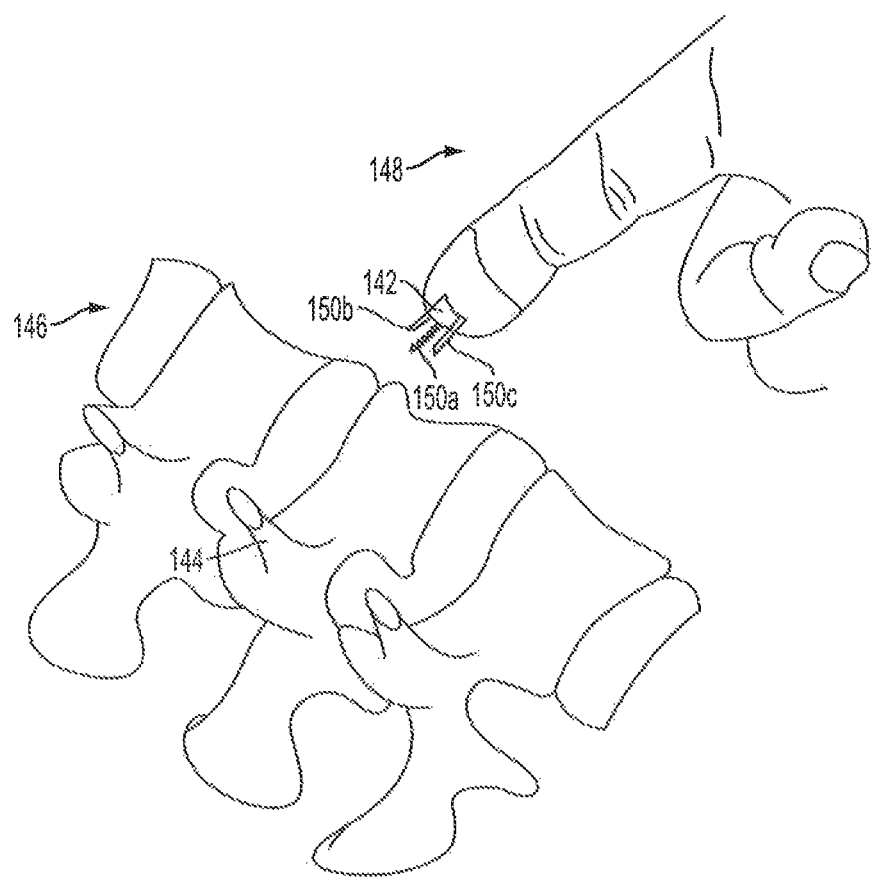
FIG. 8 is a perspective view of an embodiment of attaching a radio frequency module to a vertebra of a patient.
Figure 9:
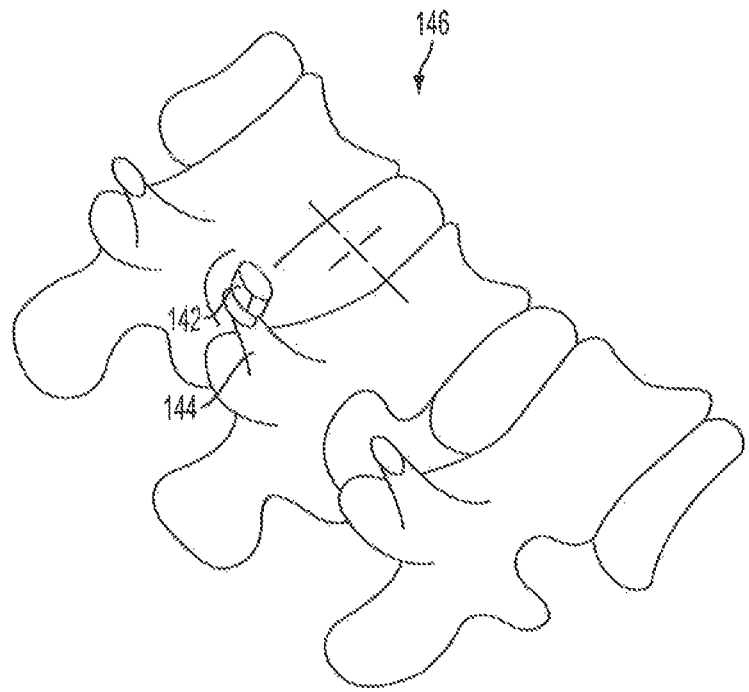
FIG. 9 is a perspective view showing the radio frequency module of FIG. 8 attached to the vertebra.

FIGS. 8 and 9 illustrate one embodiment of implanting a patient RF module 142 within a patient by attaching the patient RF module 142 to a vertebra 144 of a spine 146 of the patient. For a lateral surgical approach, the patient RF module 142 can be attached to a lateral border of a transverse process of a vertebral body, which can facilitate use of the patient RF module 142 in determining instrument trajectory without the patient RF module 142 interfering with the lateral approach access to the surgical site. As shown in FIG. 8, the patient RF module 142 can be implanted by a hand 148 of a surgeon or other medical personnel. As mentioned above, the patient RF module 142 can include one or more attachment elements configured to facilitate attachment of the patient RF module 142 to the vertebra 144. In the illustrated embodiment, the patient RF module 142 includes three attachment elements in the form of first, second, and third pins 150a, 150b, 150c, although the patient RF module 142 can include any number of attachment elements that can each be the same as or different from any of the patient RF module's other attachment elements. In the illustrated embodiment, the first pin 150a has a plurality of bone-engaging features in the form of ridges extending circumferentially therearound along a longitudinal length of the first pin 150a. The bone-engaging features can help secure the first pin 150a within the vertebra 144 and help prevent the first pin 150a from backing out of the vertebra 144. Other examples of bone-engaging features include a thread and a textured surface. The second and third pins 150b, 150c are positioned on opposite sides of the first pin 150a in the illustrated embodiment and lack bone-engaging features. The second and third pins 150b, 150c being positioned on opposed sides of the first pin 150a can help prevent the patient RF module 142 from rotating about the first pin 150a when each of the pins 150a, 150b, 150c extend at least partially into the vertebra 144. Each of the first, second, and third pins 150a, 150b, 150c can have pointed distal tips, as in the illustrated embodiment, which can facilitate penetration of the first, second, and third pins 150a, 150b, 150c into a bone such as the vertebra 144.

Figure 10:
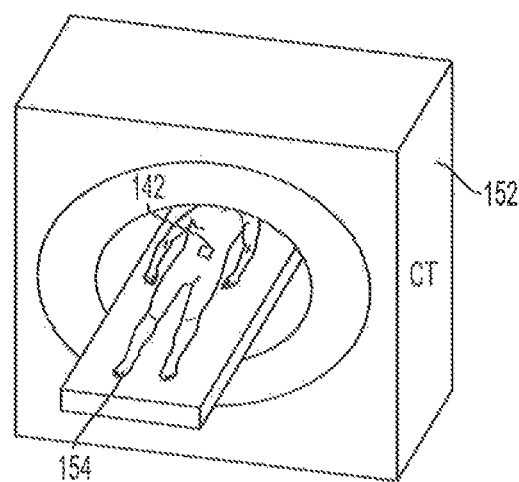
FIG. 10 is a perspective view of an embodiment of a CT scanning machine configured to gather pre-operative patient image information.

FIG. 10 illustrates an embodiment of obtaining a pre-operative image of a patient 154 using a CT scanning machine 152. However, as mentioned above, pre-operative images of a patient can be obtained in addition to or instead of CT images, such as by using other technologies such as x-ray. FIG. 10 shows the single patient RF module 142 of FIG. 9. The single RF module 142 of FIG. 9 is implanted within the patient 154 in the illustrated embodiment and would thus be invisible from an exterior of the patient 154 but is visibly shown in FIG. 10 for clarity of illustration. Also, the patient RF module 142 is shown in the illustrated embodiment as being attached to the vertebra 144 in advance of a spinal surgical procedure to be subsequently performed on the patient 154, but as mentioned above, patient RF modules can be implanted in a variety of locations, can be attached to a variety of different patient anatomies, and can be used in a variety of types of surgical procedures. As will be appreciated by a person skilled in the art, the CT scanning machine 152 can obtain one or more images of the patient 154. The one or more obtained images can be stored in the pre-planning database 206. The CT scanning machine 152 can be configured to directly transmit the one or more obtained images for storage in the pre-planning database 206, or the CT scanning machine 152 can be configured to indirectly transmit the one or more obtained images for storage in the pre-planning database 206 by first transmitting the one or more obtained images to another device, such as a desktop computer or a server configured to store the one or more obtained images in the pre-planning database 206. As discussed further below, the one or more obtained images can be used by the pre-planning module 200 in pre-determining a trajectory of a surgical instrument to be used in performing the spinal surgery on the patient 154 and/or can be used by the determination module 202 in determining an actual trajectory of the surgical instrument as the instrument is being used in performing the spinal surgery on the patient 154.

Referring again to FIG. 2, each of the one or more instrument RF modules 214 can also have a variety of sizes, shapes, and configurations. If the system 100 includes a plurality of instrument RF modules 214, each of the plurality of instrument RF modules 214 can be the same as or different from any one or more of the other instrument RF modules 214. In general, the at least one instrument RF module 214 can be configured to be attached to a surgical instrument and to wirelessly communicate using radio frequency electromagnetic fields, which can allow the instrument RF module(s) 214 to be queried without requiring a visual line of sight to the instrument RF module(s) 214. The instrument RF module(s) 214 can be configured to wirelessly transmit a signal in response to a wireless signal transmitted by an external source, such as the RF controller 216. The signal transmitted by each of the instrument RF module(s) 214 can include one or more types of data associated with the instrument RF module(s) 214, such as RF-specific information (e.g., an identifier uniquely identifying the RF module such as an identification code or name, date of the RF module's attachment to the instrument, etc.) and/or instrument-specific information (e.g., an identifier uniquely identifying the instrument such as an identification code or name, a timestamp and/or datestamp of the RF query of the instrument RF module, etc.). The data transmitted by each of the instrument RF module(s) 214 can be stored in an on-board memory of the instrument RF module(s) 214. The instrument RF module(s) 214 can each include an on-board power source, e.g., a battery, or can be powered by an external source. The instrument RF module(s) 214 can be biocompatible so as to be configured to be safely used with the patient, although the instrument RF module(s) 214 need not be biocompatible, such as if the instrument RF module(s) 214 are embedded within an instrument. In an exemplary embodiment, the instrument RF module(s) 214 can be biocompatible and can lack an on-board power source. Examples of instrument RF module(s) 214 include the RFID tags mentioned above with respect to the patient RF module(s) 212.

The one or more instrument RF module(s) 214 can be attached to the instrument in a variety of ways. In an exemplary embodiment, the instrument RF module(s) 214 can be attached to a non-movable location of the instrument, e.g., not within a part of the instrument that moves relative to another part of the instrument such as a rotatable knob, a movable lever, a translating rod, etc. In this way, the instrument RF module(s) 214 can be configured to remain at a fixed, predictable location, thereby allowing the instrument RF module(s) 214 to provide consistent locational information. The instrument RF module(s) 214 can be attached to a proximal portion of the instrument that is configured to be located outside a patient's body during use of the instrument on a patient, such as in a handle of the instrument, and/or the instrument RF module(s) 214 can be attached to a distal portion of the instrument that is configured to be located within the patient's body during use of the instrument on a patient. In an exemplary embodiment, all of the one or more instrument RF modules 214 can be attached along a longitudinal axis of the instrument and hence be positioned along a trajectory of the instrument. The one or more RF modules 214 can thus be configured to provide locational information of the instrument's trajectory. The one or more RF modules 214 can be positioned anywhere along the instrument's longitudinal axis. In an exemplary embodiment, the one or more RF modules 214 can be attached along the instrument's longitudinal axis at an elongate shaft of the instrument that defines the instrument's longitudinal axis and/or at a handle of the instrument.

In an exemplary embodiment, the instrument RF module(s) 214 can be attached to an exterior surface of the instrument. The instrument RF module(s) 214 can be attached to the exterior surface of the instrument in a variety of ways, and can be attached thereto temporarily or permanently. Temporarily attaching the instrument RF module(s) 214 to the instrument can facilitate re-use of the instrument RF module(s) 214 by allowing the instrument RF module(s) 214 to be removed from the instrument after use of the instrument and subsequently attached to another instrument. In this way, the instrument RF module(s) 214 can, but need not be, disposed of if attached to a one-time-use, disposable instrument or of the instrument to which the instrument RF module(s) 214 is attached to breaks and cannot be reused in a subsequent surgical procedure. The instrument RF module(s) 214 can be temporarily attached to the instrument using any one or more attachment elements such as a biocompatible adhesive (e.g., a glue, etc.), Velcro®, etc. In one embodiment, the instrument RF module(s) 214 can be temporarily attached to an instrument by being included in a removable component of the instrument, such as by being included in a handle configured to be removably coupled to a remainder of the instrument (e.g., by being threaded thereon, by being snap fit thereon, etc.). The removable component including the instrument RF module(s) 214 can thus be reused with various instruments, while the remainder of the instrument can be disposed of. Permanently attaching the instrument RF module(s) 214 to the external surface of the instrument can facilitate tracking of the instrument by keeping the same instrument RF module(s) attached thereto. The instrument RF module(s) 214 can be permanently attached to the instrument by being, e.g., welded to the instrument, adhered thereto using a permanent adhesive, etc.

In another exemplary embodiment, the instrument RF module(s) 214 can be permanently embedded within an instrument. Embedding the instrument RF module(s) 214 can help protect the instrument RF module(s) 214 from damage by preventing the instrument RF module(s) 214 from being exposed to on the instrument's exterior surface where fluids, sharp objects, etc. could potentially damage the instrument RF module(s) 214. The instrument RF module(s) 214 can be embedded in the instrument a variety of ways, as will be appreciated by a person skilled in the art, such as by being included within the instrument during manufacturing of the instrument.

If a plurality of instrument RF modules 214 are attached to an instrument, all of the instrument RF modules 214 can be temporarily attached to the instrument, all of the instrument RF modules 214 can be permanently attached to the instrument, or at least one of the instrument RF modules 214 can be temporarily attached and at least one of the instrument RF modules 214 can be permanently attached.

Figure 11:
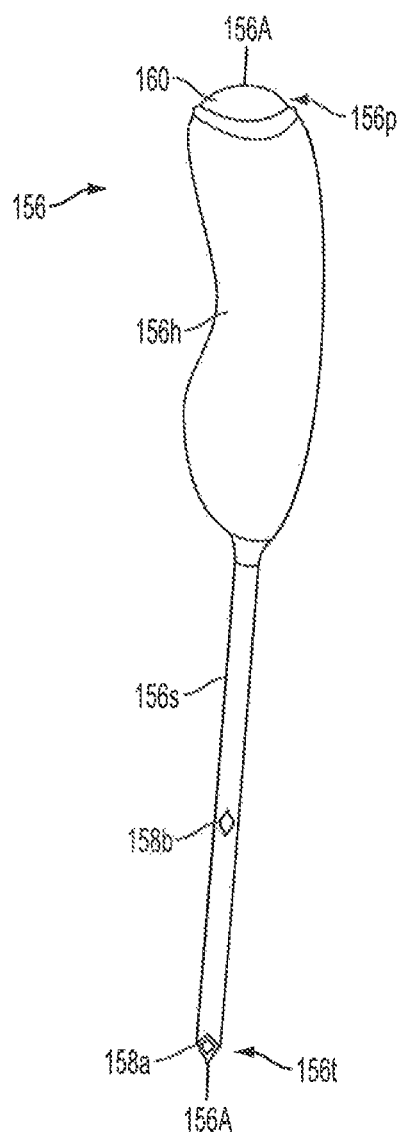
FIG. 11 is a perspective view of a surgical instrument having a plurality of radio frequency modules attached thereto.

FIG. 11 illustrates one embodiment of a surgical instrument 156 having first and second instrument RF modules 158a, 158b attached thereto. The instrument 156 illustrated in FIG. 11 includes an awl, but one or more instrument RF modules can be attached to any type of surgical instrument, such as trocars, cannulas, drills, passing pins, cross pins, spinal surgical instruments (e.g., spinal disc preparing instruments such as trials, spreaders, cobbs, etc.; retractors, inserters; etc.), etc. Although two instrument RF modules 158a, 158b are attached to the instrument 156 in the illustrated embodiment, any number of instrument RF modules can be attached to an instrument, as mentioned above. The first instrument RF module 158a is attached to an external surface of a distal tip 156t of the instrument 156 along a longitudinal axis 156A of the instrument, and the second instrument RF module 158b is attached to an external surface of an elongate shaft 156s of the instrument 156 along the instrument's longitudinal axis 156A. The RF modules 158a, 158b in the illustrated are thus attached to the instrument 156 along a trajectory of the instrument 156 defined by the longitudinal axis 156A.

The instrument 156 also includes a notification unit 160 attached thereto. The notification unit 160 includes a light located at proximal tip 156p of a handle 156h of the instrument 156. Being located at the instrument's proximal tip 156p can help the notification unit 160 remain visible even when instrument 156 is in use in a surgical procedure, e.g., when the instrument 156 is at least partially disposed within a patient. The notification unit 160 can, however, be located elsewhere on the instrument 156 and can be in a form other than a light. The notification unit 160 can be configured to provide a notification of the instrument's trajectory relative to a predetermined trajectory. The notification unit 160 can be configured to provide a notification in different degrees of precision, as discussed further below. In the illustrated embodiment, the notification unit 160 is configured to provide notification in three degrees of precision, each indicated by a differently colored light. The at least three degrees of precision can include the instrument 156 being along the predetermined trajectory as shown by a green light, the instrument 156 being near but not along the predetermined trajectory as shown by a yellow light, and the instrument being far from the predetermined trajectory as shown by a red light. Green, yellow, and red are examples; the degrees of precision can be shown by other colors.

Referring again to FIG. 2, the pre-planning module 200 can be configured to facilitate determination of the predetermined trajectory in a variety of ways using at least the one or more patient RF modules 210 attached to the patient. In general, the pre-planning module 200 can be configured to use the location(s) of the one or more patient RF modules 210 attached to the patient to determine a trajectory of an instrument to be advanced to a target surgical site. The one or more patient RF modules 210 can be attached to the patient adjacent the target surgical site, as discussed further below, which can facilitate this determination of the predetermined trajectory.

Figure 12:
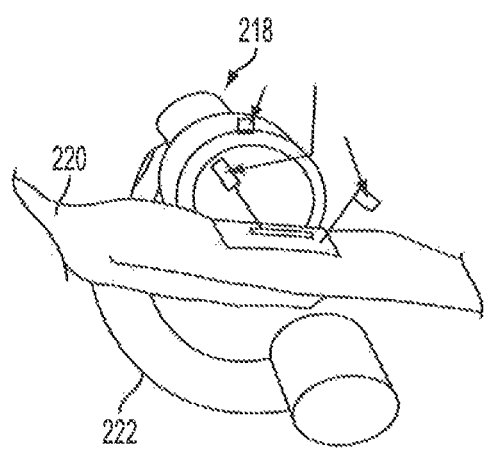
FIG. 12 is a perspective view of an embodiment of a fluoroscopy system configured to gather patient image information in a surgical setting.

The pre-planning module 200 can be configured to determine the predetermined trajectory using the one or more patient RF modules 210 attached to the patient and the one or more instrument RF modules 212 attached to the instrument. In an exemplary embodiment, the pre-planning module 200 can be configured to determine the predetermined trajectory during the surgical procedure, e.g., when the patient is in the OR or other surgical setting. After the one or more patient RF modules 210 have been attached to the patient, a user of the instrument can position the instrument at a first trajectory relative to the patient. The instrument's position relative to the patient can be verified using one or more confirmation mechanisms, as will be appreciated by a person skilled in the art, such as by taking one or more intra-operative fluoroscopy images. FIG. 12 illustrates an embodiment of a fluoroscopy system 218 configured to gather real time images of a patient 220 in an OR or other surgical setting using a C-arm 222, as will be appreciated by a person skilled in the art. Based on the verified position of the instrument relative to the patient, the instrument's first trajectory can be adjusted any number of times, with verifications of each adjusted trajectory being taken as discussed above, until the instrument is at a desired trajectory relative to the patient.

Referring again to FIG. 2, the user can signal to the pre-planning module 200 that the instrument is at the desired trajectory. The signal can be provided in any of a variety of ways, such as by the user or other personnel actuating an actuator that causes a signal to be transmitted to the pre-planning module 200. The actuator can have a variety of configurations, such as a pushable button on the instrument or other object (e.g., a keyboard button, a button on a tablet computer, etc.), a flippable switch on the instrument or other object, a voice-activated module configured to actuated with a voice command, etc.

In response to the signal transmitted to the pre-planning module, the pre-planning module 200 can be configured to set the desired trajectory as the predetermined trajectory. The pre-planning module 200 can be configured to set the predetermined trajectory in a variety of ways, such as by registering a location of the instrument at the desired trajectory using the one or more instrument RF modules 212 attached to the instrument and the one or more patient RF modules 210 attached to the patient. The location of the instrument can be registered in a variety of ways, as will be appreciated by a person skilled in the art, such as by each of the patient and instrument RF modules 210, 212 transmitting an RF signal to the pre-planning module 200 in response to a query signal, e.g., an RF signal transmitted by the RF controller 216. The pre-planning module 200 can determine the instrument's spatial relationship to the patient using any one or more techniques, such as by RFID triangulation, e.g., using an algorithm to localize the patient and instrument RF modules 210, 212. The pre-planning module 200 can be configured to set or "lock in" the determined spatial relationship of the instrument relative to the patient as the predetermined trajectory.

In another exemplary embodiment, the pre-planning module 200 can be configured to determine the predetermined trajectory before commencement of the surgical procedure, e.g., before the patient is in the OR or other surgical setting. The instrument's position relative to the patient thus need not be verified using one or more confirmation mechanisms, e.g., fluoroscopy, during performance of the surgical procedure, which can save time, reduce costs, reduce radiation exposure of the patient, and/or reduce radiation exposure of surgical personnel.

In one embodiment, the pre-planning module 200 can be configured to use the one or more patient RF modules 210 attached to the patient and one or more pre-operative images of the patient, e.g., CT image(s) of the patient gathered by the CT scanning machine 152, that include the patient RF module(s) 210 to determine the predetermined trajectory before commencement of the surgical procedure. The one or more instrument RF modules 212 attached to the instrument need not be used in this embodiment of determining the predetermined trajectory. The one or more patient RF modules 210 in this embodiment can include a single patient RF module 210 attached to a non-movable location within the patient at a target surgical site, as discussed above. The pre-planning module 200 can be configured to predetermine the trajectory based on the known location of the one patient RF module 210 attached to the patient at the target surgical site, e.g., on the target site as discussed above. The location can be known in comparison to the pre-operative image(s), which can be scaled to facilitate the comparison. The trajectory determination can include a surgeon and/or other medical personnel measuring a distance from the patient RF module 210, e.g., graphically measuring the distance. The measured distance can be entered into a programmable interface on or otherwise coupled to the surgical instrument, and the interface can set the desired spatial relationship required between the patient RF module 210 and the one or more instrument RF modules 212 to determine the trajectory. The trajectory determination can be geometric, based on establishing patient coordinates and scale, and then superimposing the trajectory associated with optimal surgical outcome results, or by surgeon preference override, for a given surgical technique. As will be appreciated by a person skilled in the art, various pre-operative planning software solutions exist that can predetermine such a trajectory based on a known target site such as image guidance software systems available from BrainLab of Feldkirchen, Germany.

In another embodiment, the pre-planning module 200 can be configured to determine the predetermined trajectory pre-surgery using the one or more patient RF modules 210 attached to the patient and one or more pre-operative images of the patient, e.g., CT image(s) of the patient gathered by the CT scanning machine 152, that include the patient RF module(s) 210. The one or more instrument RF modules 212 attached to the instrument need not be used in this embodiment of determining the predetermined trajectory. The one or more patient RF modules 210 in this embodiment can include a plurality of patient RF module 210 each attached to a non-movable location within the patient next to a target surgical site, as discussed above, such as one patient RF module 210 on each vertebra immediately adjacent to a target vertebra. The pre-planning module 200 can be configured to predetermine the trajectory based on the known location of the plurality of patient RF modules 210 attached to the patient near the target surgical site, as known by the pre-operative image(s). As will be appreciated by a person skilled in the art, various pre-operative planning software solutions exist that can predetermine such a trajectory based on a known target site, as discussed above.

The determination module 202 can be configured to determine whether the instrument's trajectory is aligned with the predetermined trajectory in a variety of ways using the one or more patient RF modules 210 attached to the patient and the one or more instrument RF modules 212 attached to the instrument. In general, the determination module 202 can be configured to compare the instrument's trajectory to the predetermined trajectory so as to determine whether the trajectory matches the predetermined trajectory. The determination module 202 can be configured to store determined trajectory information in the procedure database 208, which can facilitate review of the surgical procedure, e.g., for efficiency purposes.

The determination module 202 can be configured to compare the trajectory with the predetermined trajectory in at least two degrees of precision. In this way, the determination module 202 can be configured to indicate via the notification module 204 and the notification unit 210 one of at least one of two different positions of the trajectory of the instrument relative to the predetermined trajectory. In an embodiment including two degrees of precision, one degree of precision can indicate that the instrument's trajectory is along the predetermined trajectory, and the other degree of precision can indicate that the instrument's trajectory is not along the predetermined trajectory. In an exemplary embodiment, the determination module 202 can be configured to compare the trajectory with the predetermined trajectory in at least three degrees of precision. Allowing at least three degrees of precision can allow the notification to provide more specific information than the two degrees of "yes" or "no" as to whether the trajectory aligns with the predetermined trajectory, which can help the trajectory be more quickly and accurately adjusted to match the predetermined trajectory. The at least three degrees of precision can include the instrument being along the predetermined trajectory, the instrument being near but not along the predetermined trajectory, and the instrument being far from the predetermined trajectory. The notification can thus indicate whether the instrument should be adjusted to match the instrument's trajectory to the predetermined trajectory.

The determination module 202 can be configured to determine that the trajectory matches the predetermined trajectory without any degree of error, e.g., a 100% match. However, the determination module 202 can be configured to determine in a first degree of precision that the trajectory matches the predetermined trajectory with an amount of negligible offset, similar to allowance of machine tolerances in manufacturing parts. Allowing the amount of negligible error can better allow the determination module 202 to ever determine a match, as negligible offset may exist between the trajectory and the predetermined trajectory yet be substantially the same, as will be appreciated by a person skilled in the art. The negligible offset can be pre-programmed into the determination module 202 for each instrument used in a surgical procedure which includes one or more instrument RF modules, thereby allowing permissible negligible offset for each predetermined trajectory to be specifically accounted for by the determination module 202. Alternatively, the negligible offset can be standardized for each instrument that includes one or more instrument RF modules, which can help save planning resources. The negligible offset can be, e.g., up to about +/−2 mm from a starting point of the predetermined trajectory, up to about +/−1 mm from a starting point of the predetermined trajectory, up to about 2° away from a true center of the predetermined trajectory, up to about 1° away from a true center of the predetermined trajectory, etc.

The determination module 202 can be configured to determine in a second degree of precision that the trajectory is near but not along the predetermined trajectory, e.g., is offset from the predetermined trajectory up to a certain amount of offset. The certain amount of offset can be pre-programmed into the determination module 202 for each instrument used in a surgical procedure which includes one or more instrument RF modules, thereby allowing permissible offset for each predetermined trajectory to be specifically accounted for by the determination module 202. Alternatively, the certain amount of offset can be standardized for each instrument that includes one or more instrument RF modules 214, which can help save planning resources. The certain amount offset can be, e.g., greater than the negligible offset and less than about +/−4 mm from a starting point of the predetermined trajectory, greater than the negligible offset and less than about +/−3 mm from a starting point of the predetermined trajectory, greater than the negligible offset and less than about 5° away from a true center of the predetermined trajectory, etc.

The determination module 202 can be configured to determine in a third degree of precision that the instrument's trajectory is far from the predetermined trajectory, e.g., is offset from the predetermined trajectory over the certain amount of offset. The determination module 202 can be configured to determine that the trajectory is offset from the predetermined trajectory over the certain amount of offset if the instrument's trajectory is offset, e.g., greater than about +/−4 mm from a starting point of the predetermined trajectory, greater than about +/−3 mm from a starting point of the predetermined trajectory, greater than about 5° away from a true center of the predetermined trajectory, etc.

Although three degrees of precision are described above, the determination module 202 can be configured to compare the trajectory to the predetermined trajectory in more than or less than three degrees. Each different degree of precision that the determination module 202 is configured to use can have a different range of offset. In other words, a first degree of precision can be within "A" offset, a second degree of precision can be greater than "A" offset but less than "B" offset, a third degree of precision can be greater than "B" offset but less than "C" offset, a fourth degree of precision can be greater than "C" offset but less than "D" offset, etc.

The determination module 202 can be configured to compare the predetermined trajectory with a trajectory of the instrument having one or more RF modules 214 attached thereto and for at least one additional surgical instrument used on the patient that has one or more instrument RF modules 214 attached thereto. The predetermined trajectory determined for one instrument by the pre-planning module 200 can thus be used for multiple instruments without having to determine a predetermined trajectory for each of the different instruments.

The determination module 202 can be configured to cause the notification module 204 to trigger the notification unit 210 to provide the notification in at least two degrees of precision. If the notification indicates that the instrument is along the predetermined trajectory, e.g., the determination module 202 determines that the trajectory matches the predetermined trajectory, then the instrument can be maintained in its current trajectory. If the notification indicates that the instrument is near but not along the predetermined trajectory, e.g., the determination module 202 determines that the trajectory is offset from the predetermined trajectory up to the certain amount of offset, the instrument can be slightly adjusted to align its trajectory with the predetermined trajectory. In other words, a user of the instrument can be notified that the instrument only needs slight adjustment to be aligned with the predetermined trajectory, which can help prevent the user from overcorrecting to align with the predetermined trajectory. If the notification indicates that the instrument's trajectory is far from the predetermined trajectory, e.g., the determination module 202 determines that the trajectory is offset from the predetermined trajectory over the certain amount of offset, the instrument can be adjusted in a relatively aggressive manner to align its trajectory with the predetermined trajectory. In other words, a user of the instrument can be notified that the instrument needs a relative large amount of adjustment to be aligned with the predetermined trajectory, which can help prevent the user more quickly align the instrument's trajectory with the predetermined trajectory than if the user was merely informed that the instrument's trajectory is not aligned with the predetermined trajectory.

The determination module 202 can be configured to cause the notification module 204 to trigger the notification unit 210 to provide a different notification for each of the different degrees of precision, e.g., a different sound for each degree of precision (e.g., one beep for a first degree, two beeps for a second degree, three beeps for a third degree, etc.; a chime for a first degree, a buzz for a second degree, a click for a third degree, etc.; and so forth), a different colored light for each degree of precision (e.g., a green light for a first degree, a yellow light for a second degree, a red light for a third degree, etc.; no light for a first degree, a white light for a second degree, a red light for a third degree, etc.; and so forth), a different light illumination sequence for each degree of precision (e.g., one light blink for a first degree, two light blinks for a second degree, three light blinks for a third degree, etc.; a steady light for a first degree, a slowly blinking light for a second degree, a faster blinking light for a third degree, etc.; and so forth), different text digitally shown on a display for each degree of precision (e.g., "no adjustment needed" for a first degree, "slight adjustment needed" for a second degree, "significant adjustment needed" for a third degree; and so forth), different vibration for each degree of precision (e.g., no vibration for a first degree, slight vibration for a second degree, significant vibration for a third degree, etc.; and so forth), etc.

The determination module 202 can be configured to cause the notification module 204 to trigger the notification unit 210 to provide only one type of notification (e.g., one of sounds, light, vibration, text, etc.), or the determination module 202 can be configured to cause the notification module 204 to trigger the notification unit 210 to simultaneously provide a plurality of types of notification (e.g., two or more of sounds, light, vibration, text, etc.). Providing multiple types of notifications can help increase chances that the notification is detected, e.g., seen, heard, and/or felt, by a user of the instrument, thereby increasing chances that the instrument's trajectory matches the predetermined trajectory throughout use of the instrument.

In use, the system 100 can be configured to identify whether a surgical instrument being used in a surgical procedure on a patient has a trajectory relative to the patient that is aligned with a predetermined trajectory, and to provide notification of the trajectory's alignment relative to the predetermined trajectory. An embodiment of trajectory identification is discussed below with reference to an embodiment of a surgical procedure illustrated in FIGS. 13 and 14, the module 200, 202, 204 of FIG. 2, the patient RF module 142 and the patient 154 of FIGS. 8-10 and the instrument 156 and the instrument RF modules 158a, 158b of FIG. 11. However, any of the computer systems described herein can be configured to provide such trajectory identification, and the trajectory identification can be provided in connection with any of a variety of surgical procedures in which it is beneficial to advance a surgical instrument toward a patient at a particular approach angle, e.g., so that the instrument accesses a target site at an angle from which the instrument can perform its desired function, so that the instrument is inserted into the patient without damaging any patient's nerves, so that the instrument's trajectory matches a trajectory identified by a surgeon pre-surgery, etc.

Figure 13:
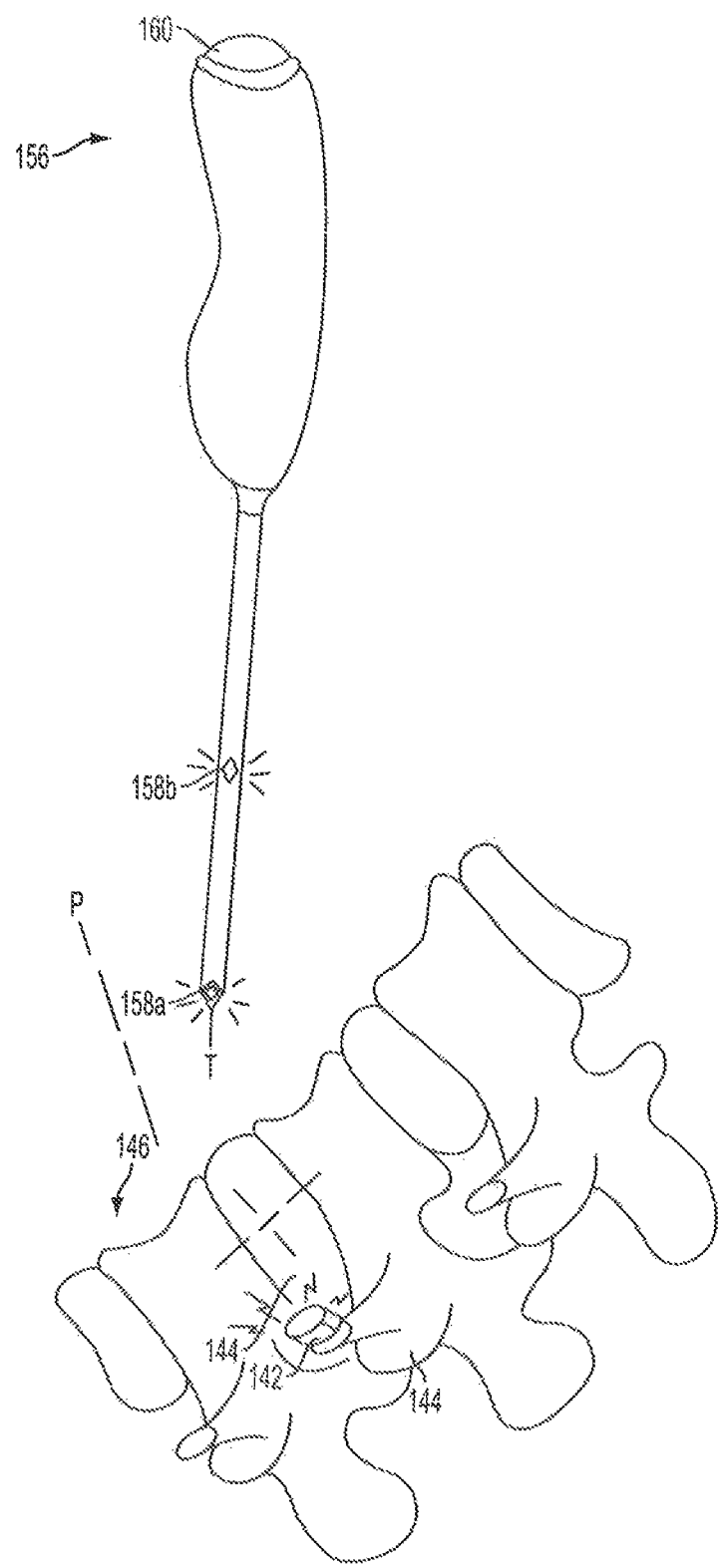
FIG. 13 is a perspective view of the instrument of FIG. 11 in a vicinity of the vertebra of FIG. 9 at a first trajectory relative to the spine.

The instrument 156 can be advanced toward the spine 146 of the patient 154, as shown in FIG. 13. If a predetermined trajectory P has not already been determined by the pre-planning module 200, the predetermined trajectory P can be determined by the pre-planning module 200, as discussed above. The determination module 202 can determine whether a trajectory T of the instrument is aligned with the predetermined trajectory P in any number of ways, as discussed above. The determination module 202 can determine that the trajectory T is not aligned with the predetermined trajectory P, as shown in FIG. 13. The determination module 202 can thus not cause the light 160 to light up. In other words, the light 160 not being illuminated can indicate that the trajectory T is not aligned with the predetermined trajectory P. The determination module 202 thus does not cause the notification module 204 to trigger illumination of the light 160.

Figure 14:
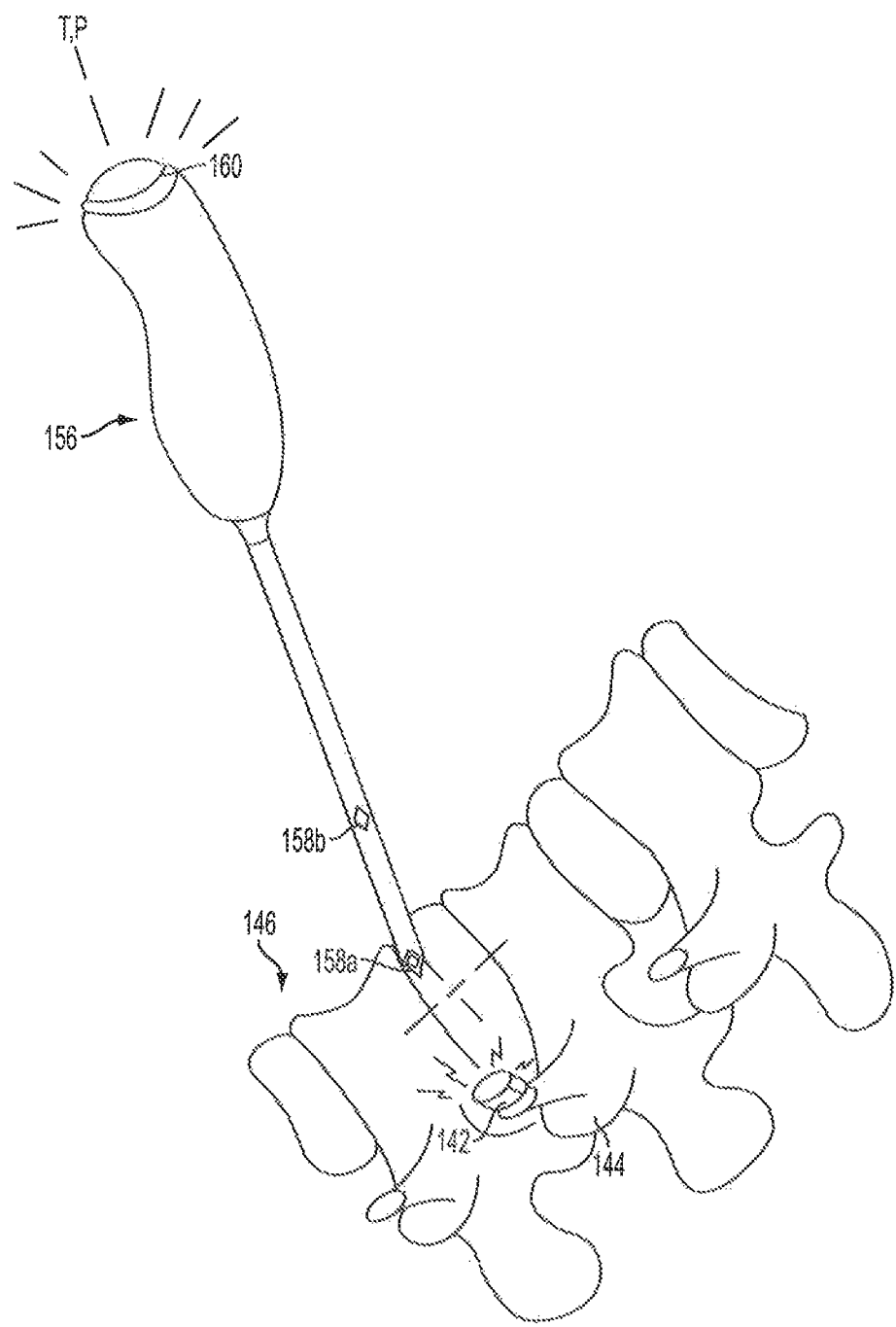
FIG. 14 is a perspective view of the instrument of FIG. 13 at a second, different trajectory relative to the spine.

The instrument 156 can be adjusted in position relative to the patient 154, with the determination module 202 repeatedly determining whether the trajectory T is aligned with the predetermined trajectory P. The repeated determinations can be continuous, which can allow the notification unit 410, e.g., the light 160, to provide continuously updated trajectory information, thereby allowing the trajectory T to be readjusted based on substantially real time information. Alternatively, the determination module 202 can be configured to repeatedly compare the trajectory T with the predetermined trajectory P at predetermined intervals, e.g., every 0.5 seconds, every one second, every two seconds, etc., which can help conserve processing resources of the system 10. When the determination module 202 determines that the trajectory T is aligned with the predetermined trajectory P, as shown in FIG. 14, the determination module 202 can cause the notification module 204 to trigger illumination of the light 160. The determination module 202 can continue monitoring the trajectory T relative to the predetermined trajectory P so as to change the notification, e.g., cause the notification module 204 to turn off the light 160 or change the light 160 to another color, if the trajectory T becomes misaligned from the predetermined trajectory P. The predetermined trajectory P can be readjusted any number of times during the surgical procedure, e.g., if a surgeon decides that another angular approach would be appropriate.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
a first radio frequency module configured to be attached to a patient at a non-movable location relative to the patient;
a surgical instrument having a handle configured to be grasped by a user at a proximal end of the instrument, a second radio frequency module attached at a distal end of the instrument, and a third radio frequency module spaced proximally from the distal end and attached along an elongate shaft of the instrument that defines the instrument's longitudinal axis;
an actuator configured to be actuated by a user when the surgical instrument is positioned at a desired trajectory angle relative to a target site within the patient to set a spatial relationship between the first, second and third radio frequency modules as a predetermined trajectory to the target site; and
a notification module configured to provide a notification to a user of the surgical instrument whether the surgical instrument is positioned along the predetermined trajectory based on a determined position of the second and third radio frequency modules relative to the first radio frequency module.

2. The system of claim 1, wherein the notification module is configured to indicate whether the surgical instrument is positioned along the predetermined trajectory in at least three degrees of precision, the three degrees of precision including the surgical instrument being along the predetermined trajectory, the surgical instrument being near but not along the predetermined trajectory, and the surgical instrument being far from the predetermined trajectory.

3. The system of claim 1, wherein the notification module is configured to indicate whether the surgical instrument is positioned along the predetermined trajectory using at least one of an audio signal, a vibration of the surgical instrument, a light, and text.

4. The system of claim 1, wherein the notification module is configured to repeatedly provide the notification to the user so as to repeatedly provide feedback to the user regarding whether the surgical instrument is positioned along the predetermined trajectory as the surgical instrument is being moved relative to the patient.

5. The system of claim 1, further comprising a determination module configured to repeatedly determine the position of the second and third radio frequency modules relative to the first radio frequency module so as to repeatedly determine whether the surgical instrument is positioned along the predetermined trajectory, the notification module being configured to continuously provide the notification to the user so as to continuously provide feedback to the user regarding whether the surgical instrument is positioned along the predetermined trajectory.

6. The system of claim 1, further comprising a processor configured to:
be in communication with the first radio frequency module, the second radio frequency module, the third radio frequency module, and the notification module;
determine the position of the surgical instrument relative to the first radio frequency module; and
cause the notification module to provide the notification.

7. The system of claim 1, wherein the non-movable location relative to the patient comprises a bone.

8. The system of claim 7, wherein the bone comprises a vertebral body, and the non-movable location relative to the patient comprises a lateral border of a transverse process of the vertebral body.

9. A surgical method, comprising:
implanting a first radio frequency module within a patient at a target site;
positioning a surgical instrument having second and third radio frequency modules attached thereto at a desired trajectory with respect to the target site using fluoroscopic imaging;
actuating an actuator when the surgical instrument is positioned at the desired trajectory to set a spatial relationship between the first, second, and third radio frequency modules as a predetermined trajectory to the target site;
moving the surgical instrument toward the target site along a trajectory;
determining a position of the second and third radio frequency modules relative to the first radio frequency module so as to determine whether the trajectory along which the surgical instrument is being moved is along the predetermined trajectory to the target site within the patient; and
providing a notification to a user of the surgical instrument whether the surgical instrument is being moved along the predetermined trajectory.

10. The method of claim 9, further comprising resetting the predetermined trajectory by positioning the surgical instrument at a second desired trajectory relative to the target site and setting a spatial relationship between the first, second, and third radio frequency modules when the surgical instrument is at the second desired trajectory as the predetermined trajectory.

11. The method of claim 9, further comprising:
attaching a fourth radio frequency module to the patient at a non-movable location relative to the patient; and
setting a spatial relationship between the first, second, third, and fourth radio frequency modules as the predetermined trajectory.

12. The method of claim 9, wherein the target site comprises a spinal disc level.

13. The method of claim 9, wherein the notification is continuously provided to the user so as to continuously provide feedback to the user regarding whether the surgical instrument is being moved along the predetermined trajectory as the surgical instrument is being moved relative to the patient.

14. The method of claim 9, further comprising repeatedly determining the position of the second and third radio frequency modules relative to the first radio frequency module so as to repeatedly determine whether the surgical instrument is being moved along the predetermined trajectory, the notification being continuously provided to the user so as to continuously provide feedback to the user regarding whether the surgical instrument is being moved along the predetermined trajectory.

15. The method of claim 9, further comprising:
moving a second surgical instrument toward the patient, the second surgical instrument having fourth and fifth radio frequency modules attached thereto;
determining a position of the fourth and fifth radio frequency modules relative to the first radio frequency module so as to determine whether the second surgical instrument is being moved along the predetermined trajectory; and providing a notification to a user of the second surgical instrument whether the second surgical instrument is positioned along the predetermined trajectory.

16. The method of claim 9, wherein providing the notification comprises indicating whether the surgical instrument is positioned along the predetermined trajectory in one of at least three degrees of precision, the three degrees of precision including the surgical instrument being along the predetermined trajectory, the surgical instrument being near but not along the predetermined trajectory, and the surgical instrument being far from the predetermined trajectory.

17. The method of claim 9, wherein providing the notification comprises at least one of sounding an audio signal, vibrating the surgical instrument, illuminating a light, and displaying text.

18. The method of claim 9, wherein the target site comprises a bone.

19. A surgical method, comprising:

attaching a first radio frequency module to a patient at a non-movable location relative to the patient;

moving a surgical instrument toward the patient, the surgical instrument having a proximal end having a handle configured to be grasped by a user, a shaft extending distally from the handle that defines a longitudinal axis of the instrument, a second radio frequency module attached to a distal end the shaft, and a third radio frequency module attached along the shaft, the third radio frequency module being spaced proximally a distance apart from the second radio frequency module;

determining a predetermined trajectory to a target site within the patient by positioning the surgical instrument at a desired trajectory angle relative to the target site, said desired trajectory angle being established using fluoroscopic imaging of the target site and the surgical instrument, and setting a spatial relationship between the first, second, and third radio frequency modules when the surgical instrument is at the desired trajectory angle as the predetermined trajectory;

determining a position of the second and third radio frequency modules relative to the first radio frequency module so as to determine whether the surgical instrument is being moved along the predetermined trajectory; and providing a notification to a user of the surgical instrument whether the surgical instrument is being moved along the predetermined trajectory.

20. A surgical method, comprising:

implanting a first radio frequency module in a first vertebra of a patient;

positioning a surgical instrument having a second radio frequency module attached at a distal end of the instrument and a third radio frequency module spaced proximally from the second radio frequency module and attached along an elongate shaft of the instrument that defines a longitudinal axis of the instrument at a desired trajectory with respect to the first vertebra;

actuating an actuator when the surgical instrument is positioned at the desired trajectory to set a spatial relationship between the first, second, and third radio frequency modules as a predetermined trajectory to the first vertebra, the spatial relationship being registered by each of the first, second, and third frequency modules transmitting a signal to an external receiver;

moving the instrument towards the first vertebra along a trajectory;

verifying a position of the second and third radio frequency modules relative to the first radio frequency module as the surgical instrument moves toward the first vertebra to compare the trajectory of the instrument to the predetermined trajectory to determine whether the trajectory of the instrument matches the predetermined trajectory;

providing a notification to a user of the surgical instrument, via a notification unit positioned at a proximal end of the instrument, whether the instrument is being moved along the predetermined trajectory; and adjusting the trajectory of the instrument, if the notification unit indicates that the trajectory of the instrument is not aligned with the predetermined trajectory, until the instrument is aligned with the predetermined trajectory, wherein the position of the second and third radio frequency modules relative to the first radio frequency module is verified continuously as the instrument moves toward the first vertebra.

* * * * *